United States Patent [19]

Kramer

[11] 4,332,730
[45] Jun. 1, 1982

[54] DIHALOMETHYLENELACTONE PYRETHROID INTERMEDIATES

[75] Inventor: Petrus A. Kramer, Amsterdam, Netherlands

[73] Assignee: Shell Oil Company, Houston, Tex.

[21] Appl. No.: 266,579

[22] Filed: May 22, 1981

[30] Foreign Application Priority Data

May 30, 1980 [GB] United Kingdom ................. 8017700
May 8, 1981 [EP] European Pat. Off. ........... 81200491

[51] Int. Cl.$^3$ ......................................... C07D 307/93
[52] U.S. Cl. .............................................. 549/302
[58] Field of Search ................................ 260/343.3 R

[56] References Cited

U.S. PATENT DOCUMENTS

| 3,527,769 | 9/1970 | Matsui et al. | 260/343.4 |
| 3,975,381 | 8/1976 | Kondo et al. | 260/343.6 |
| 4,083,855 | 4/1978 | Itaya et al. | 260/343.6 |
| 4,166,063 | 8/1979 | Martel et al. | 260/343.3 R |

OTHER PUBLICATIONS

Winston et al., Jour. Amer. Chem. Soc., 88:18, Sep. 20, 1966.

*Primary Examiner*—Jane T. Fan

[57] ABSTRACT

The novel dihalomethylenelactone of formula (I) can be prepared by the trihalomethylation of an anhydride of formula (II). Reaction of compound (II), wherein $R_1=R_2=$methyl, with $CBr_3COONa$ in DMF gave at $-25°$ C. the dibromovinyllactone and with $CCL_3COONa$ in DMF at $0°$ C. the dichlorovinyllactone.

$X_1$, $X_2$ and $X_3$ are halogen atoms and $R_1$ and/or $R_2$ are hydrogen atoms and/or alkyl groups with 1–10 carbon atoms;

M is alkali, e.g. Na or K. The novel dihalomethylenelactones can also be prepared by treating a compound of formula (III)

with phosphorus halide and zinc in an inert, polar aprotic solvent.

The compounds are pyrethroid intermediates.

5 Claims, No Drawings

DIHALOMETHYLENELACTONE PYRETHROID INTERMEDIATES

BACKGROUND OF THE INVENTION

1. Field of the Invention

The present invention is directed to novel dihalomethylenelactones pyrethroid intermediates and to processes for the preparation thereof.

2. Description of the Prior Art

Pyrethroids show remarkable activity against various insects. Moreover, these compounds show very low mammalian toxicity which makes them extremeley useful as pesticides for crop protection. Thus bollworm species, which infest cotton, and cotton leaf worms, which are leafeating pests, are effectively combatted with pyrethroids. Pyrethroids have shown their usefulness as pesticides for fruit and vegetables protection as well. Also for animal health protection pyrethroids can successfully be applied. For example against red mites which are found in the cracks and crevices of poultry houses, particularly on perches, and which cause loss of condition by feeding on the blood of the birds. Another application of pyrethroids is against some kinds of beatles which may cause serious structural damage to buildings, especially those containing wood or polystyrene. The proved usefulness of pyrethroids stimulates Research and Development to find novel intermediates and novel economic routes to certain cyclopropanecarboxylate pyrethroids containing a dihalovinyl group.

From Journal of the American Chemical Society /88:18/ September 20, 1966, pp. 4196-4198 it is known that the reaction of succinic anhydride with sodium trichloroaectate gives 5,5,5-trichlorolevulinic acid in dimethoxyethane. In low yield (7-8%) a side product, 5,5-dichloro-4-hydroxy-2,4-pentadienoic acid lactone (dichloroprotoanemonin) is formed. This lactone comprises a conjugated system of three double bonds.

SUMMARY OF THE INVENTION

The present dihalomethylenelactone is a novel compound with formula I

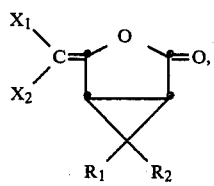

wherein $X_1$ $X_2$ are halogen atoms selected from chlorine, fluorine or bromine, and $R_1$ and/or $R_2$ are hydrogen atoms and/or alkyl groups with 1-10 carbon atoms.

The present invention therefore provides a dihalomethylenelactone with formula I

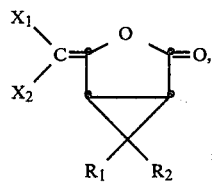

wherein $X_1$ and $X_2$ are halogen atoms and $R_1$ and/or $R_2$ are hydrogen atoms and/or alkyl groups with 1-10 carbon atoms. Preferably, $X_1$ and $X_2$ are bromine or chlorine, especially chlorine. $R_1$ and $R_2$ are preferably alkyl groups with 1-10 carbon atoms. Most preferably $R_1$ and $R_2$ are methyl.

The present invention includes isomers of the novel dihalomethylenelactones. The cis or trans optical isomer forms based on the cyclopropyl ring are usually preferred because the resulting pyrethroid esters usually have a higher pesticidal activity than the cis/trans mixtures.

The compounds of the invention may be prepared as a by-product of the process described in concurrently filed U.S. application Ser. No. 266,580 and its UK priority application No. 80/17,698, filed May 30, 1980, in which an anhydride with formula

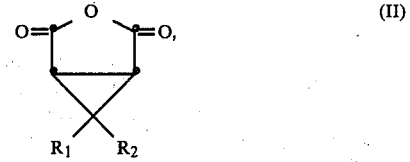

wherein $R_1$ and/or $R_2$ are hydrogen atoms and/or alkyl groups with 1-10 carbon atoms, is reacted with trihaloacetate to form a dihalomethylenelactone. This reaction gives a lactone in a yield of about 30% w. Moreover, this lactone has no conjugated system.

A process for the preparation of a chemical compound of formula (I) comprises the reaction of an anhydride with formula II

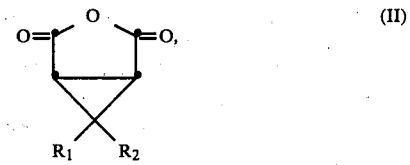

wherein $R_1$ and/or $R_2$ are hydrogen atoms and/or alkyl groups with 1-10 carbon atoms, with a trihaloacetate of formula

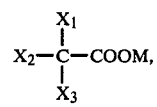

wherein $X_1$, $X_2$ and $X_3$ are halogen atoms and M is an alkali metal atom, the molar ratio of the anhydride and the trihaloacetate is in the range of from about 1:1 to about 1:5. Preferably $X_1$, $X_2$, and $X_3$ are chosen from chlorine and bromine, and M is chosen from sodium and potassium. Most preferred $X_1=X_2=X_3$ is chlorine, and M is sodium.

The temperature of the process is preferably in the range of from about $-40$ to about $80°$ C. The molar ratio of the anhydride and the trihaloacetate is preferably in the range of from about 1:1 to about 1:2. The reaction between the anhydride and the trihaloacetate is preferably carried out in an inert, polar and aprotic solvent. The term "aprotic" as used herein denotes a solvent which is free from hydrogen atoms that are able to form hydrogen bonds with anions. These definitions are in accordance with "Physical Chemistry of Organic Solvent Systems", edited by A. K. Corrington and T. Dickinson, Plenum Press (1973), pages 332 and 333.

Useful solvents are N-methylpyrrolidone, N,N-dimethylformamide and acetonitrile. Preferably the solvent N,N,-dimethylformamide is used.

Further laboratory experiments revealed a second novel process for the preparation of the present dihalomethylenelactone. Using this process even yields as high as 90% w can be achieved. This process involves the reaction of a chemical compound (a lactol) with formula III

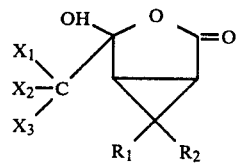

wherein $X_1$, $X_2$ and $X_3$ are halogen atoms and $R_1$ and $R_2$ are alkyl groups with 1-10 C-atoms, with phosphorus halide ($PX_3$, wherein X is a halogen atom) and zinc in an inert, polar and aprotic solvent. According to NMR spectra the compound of formula (III) appears to be in equilibrium with a keto acid of formula IV

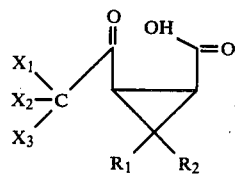

wherein $X_1$, $X_2$, $X_3$, $R_1$ and $R_2$ have the same meaning as in the lactol of formula (III). The molar ratio of the lactol and keto acid is about 20:80. Therefore the present invention also provides a process for the preparation of a chemical compound of general formula (I)

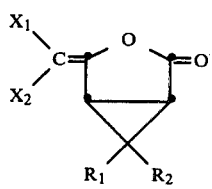

comprising the reaction of a chemical compound of general formula (III)

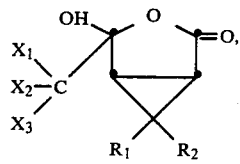

wherein $X_1$, $X_2$ and $X_3$ are halogen atoms and $R_1$ and $R_2$ are alkyl groups with 1-10 carbon atoms, with phosphorus halide ($PX_3$, wherein X is halogen selected from chlorine, bromine or fluorine) and zinc in an inert, polar aprotic solvent. Preferably $X_1$, $X_2$ and $X_3$ in chemical compound of formula (III) are chlorine, and $R_1$ and $R_2$ are preferably methyl. Preferably X in $PX_3$ is chlorine, and the inert, polar and aprotic solvent is N-methylpyrrolidone, acetonitrile or preferably N,N-dimethylformamide. The temperature at which the process is carried out is preferably in the range of from about −20° to about 100° C. or preferably from about 0° to about 100° C. The molar ratio of the compound of formula (III) and phosphorus halide is preferably in the range of from about 1:1 to about 1:4.

The molar ratio of the compound of formula (III) and zinc is preferably in the range of from about 1:1 to about 1:4.

The novel dihalomethylenelactones of the present invention are converted in to known pyrethroid intermediates, for example, by transestrification in the presence of acid, e.g. using methanol, to form a corresponding keto-acid ester of the formula

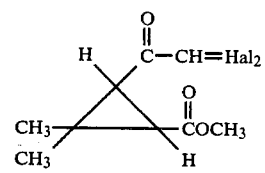

Such a keto-acid ester is known from German Pat. No. 2,639,777 along with its conversion to known dihalovinylcyclopropanecarboyxlic acid used to prepare pyrethroid esters.

EXAMPLES

The invention is further illustrated by the following examples which describe the preparation of typical species of the invention. These examples are provided for the purpose of illustration only and should not be regarded as limiting the invention in any way.

EXAMPLE I

A solution of 0.5 g caronic anhydride (3.6 mmol) and 1.34 g $CCl_3COONa$ (7.2 mmol) in 10.8 ml DMF was stirred during 3 h at 0° C. After 64 h at 7° C. the reaction mixture was acidified with concentrated hydrochloric acid, diluted with 75 ml water, extracted with $CH_2Cl_2$ (3×10 ml) and the collected $CH_2Cl_2$ extracts were washed with water (3×10 ml), dried over $MgSO_4$, filtered and the solvent was removed under reduced pressure, leaving 0.65 g of an oil. NMR analysis showed that the conversion of caronic anhydride was 70% with a selectivity to the dichloromethylene compound of 45%.

EXAMPLE II

An NMR tube was charged with a 20/80 mixture of a lactol of formula

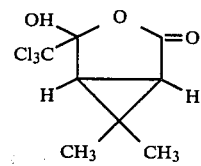

and a keto acid of formula

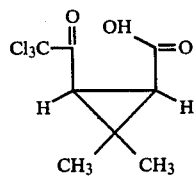

(78 mg, 0.30 mmol), 124 mg PCl$_3$ (0.90 mmol) and 0.4 ml CDCl$_3$. After 16 h at 50° C. the solvent was evaporated and the oily residue was dissolved in 0.5 ml DMF. Afterwards 39 ml Zn (0.60 mmol) was added at 20° C. and the reaction mixture was shaken during five minutes and subsequently diluted with 1 ml water, extracted with 0.4 ml CDCl$_3$, the organic phase was washed three times with 1 ml water and analysed by CLC and NMR. Conversion: 100%; selectivity: 92%.

NMR: Varian EM-390 spectrometer.

Chemical shift in ppm from TMS solvent CDCl$_3$

A and B: 1.21 (s, 3H) and 1.29 (s, 3H);
C: 2.37 (d, 1H), J$_{CD}$=6 Hz;
D: 2.85 (d, 1H).

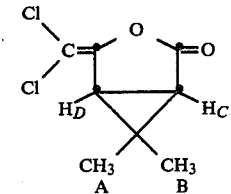

The following dibromo-methylene compound was also prepared.

A and B: 1.21 (s, 3H) and 1.28 (s, 3H);
C: 2.42 (d, 1H) J$_{CD}$=6 Hz;
D: 2.86 (d, 1H).

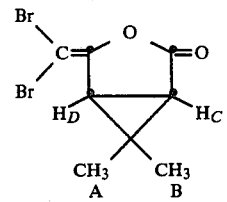

I claim:
1. A compound of formula

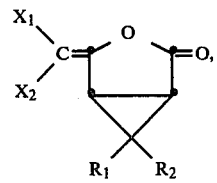

wherein X$_1$ and X$_2$ are the same or different halogen atoms, and R$_1$ and R$_2$ are the same or different and are hydrogen atoms or alkyl groups with 1-10 carbon atoms.

2. A compound according to claim 1, wherein X$_1$ and X$_2$ are chosen from chlorine and bromine.

3. A compound according to claim 2 wherein X$_1$ and X$_2$ each is chlorine.

4. A compound according to claim 1 wherein R$_1$ and R$_2$ each is an alkyl group with 1-10 carbon atoms.

5. A compound according to claim 4 wherein R$_1$ and R$_2$ each is a methyl group.

* * * * *